(12) United States Patent
Wardle et al.

(10) Patent No.: US 7,129,348 B1
(45) Date of Patent: Oct. 31, 2006

(54) POLYCYCLIC, POLYAMIDES AS PRECURSORS FOR ENERGETIC POLYCYCLIC POLYNITRAMINE OXIDIZERS

(75) Inventors: Robert B. Wardle, Logan, UT (US); Jerald C. Hinshaw, Logan, UT (US)

(73) Assignee: Alliant Techsystems Inc., Edina, MN (US)

( * ) Notice: Subject to any disclaimer, the term of this patent is extended or adjusted under 35 U.S.C. 154(b) by 1826 days.

(21) Appl. No.: 07/292,028

(22) Filed: Dec. 21, 1988

(51) Int. Cl.
*C07D 487/22* (2006.01)
*C06B 25/34* (2006.01)

(52) U.S. Cl. .................... 540/554; 540/556; 149/92
(58) Field of Classification Search ............... 540/554, 540/556; 149/92
See application file for complete search history.

(56) References Cited

U.S. PATENT DOCUMENTS

| | | | |
|---|---|---|---|
| 2,485,855 | A | 10/1949 | Blomquist et al. |
| 4,432,902 | A | 2/1984 | McGuire et al. |
| 5,124,493 | A | 6/1992 | Lukasavage et al. |
| 5,693,794 | A | 12/1997 | Nielsen ................ 540/554 |
| 5,739,325 | A | 4/1998 | Wardle et al. |
| 6,472,525 | B1 * | 10/2002 | Kodama et al. ........... 540/554 |

FOREIGN PATENT DOCUMENTS

EP          0753519 A1        1/1997

OTHER PUBLICATIONS (Classified Document (Confidential)) Polynitropolyaza Caged Explosives Part 6, A.T. Nielsen et al. Aug. 1987 Naval Weapons Ctr. China Lake C.
(Classified Document (Confidential)) Synthesis of a Caged Nitramine A.T. Nielsen Naval Weapons Ctr. China Lake, CA 93555-6001.
Polynitropolyaza Caged Explosives Part 5 Mar. 1986 Naval Weapons Ctr. China Lake, CA.
Synthesis of 2,4,6,8,10,12-Hexabenzyl-2,4,6,8,10,12-Hexaazaisowurtzitan Arnold T. Nielsen, Chemistry Division, Research Dept. Naval Weapons Ctr. China Lake CA.
Robert A W Johnstone and Anna H Wilby, *Chem. Rev.* (1985) 85 129-170.
Nielsen, Arnold T., et al., "Polyazapolycyclics by Condensation of Aldehydes with Amines. 2. Formation of 2, 4, 6, 8, 10, 12-Hexabenzyl-2, 4, 6, 8, 10, 12-hexaazatetracyclo[5.5.0.05.9.03.11]dodecanes from Blyoxal and Benzylamines 1, 2," J. Org. Chem. 1990, 55, pp. 1459-1466.
Pace, M.D.,"EPR Spectra of Photochemical NO2 Formation in Monocyclic Nitramines and Hexanitrohexaazalsowurtzitane," J. Phys. Chem. 1991, 95, pp. 5858-5864.
Pace, M.D., "Free Radical Mechanisms in High Density Nitro-Compounds: Hexanitroisowurtzitane, a New High-Energy Nitramine, " Mol. Cryst. Liq. Cryst. 1992, vol. 219, pp. 139-141 and 146-147.
Patil, D.G., et al., "Thermal Decomposition of Enegetic Materials 53. Kinetics and Mechanism of Thermolysis of Hexanitrohexaazaisowurtzitane," Combustion and Flame, 1991, vol. 87, pp. 145-147 and 150-151.
Patil, D.G., et al., "Thermal Decomposition of Energetic Materials. 59. Characterization of the Residue of Hexanitrohexaazaisowurtzitane," Combustion and Flame, 1993, vol. 92(4), pp. 456-458 (Abstract).
Russell, T.P., et al., "High-Pressure Phase Transition in Y-Hexanitrohexaazalsowurtzitane," j. phys. Chem. 1992, vol. 96, pp. 5509-5512.
Russell, T.P., et al., "Pressure/Temperature Phase Diagram of Hexanitrohexaazaisowurtzitane," J. Phys. Chem. 1993, vol. 97(9), pp. 1993-1997 (Abstract).

* cited by examiner

*Primary Examiner*—Venkataraman Balasubramanian
(74) *Attorney, Agent, or Firm*—TraskBritt

(57) ABSTRACT

Hexabenzylhexaazaisowurtzitane is converted to tetracetyl, dibenzyl azaisowurtzitane. The benzyl groups are removed by catalytic transfer hydrogenolysis leaving a pair of available nitrogens. The available nitrogens are acetylated, and the resulting intermediate is converted to CL-20 with a strong nitrating agent.

15 Claims, No Drawings

POLYCYCLIC, POLYAMIDES AS PRECURSORS FOR ENERGETIC POLYCYCLIC POLYNITRAMINE OXIDIZERS

The present invention is directed to caged nitrogen compounds, particularly derivatives of hexaazaisowurtzitane and to methods of synthesis of these compounds.

BACKGROUND OF THE INVENTION

Arnold T. Nielsen in a paper entitled "Synthesis of 2,4,6,8,10,12-Hexabenzyl-2,4,6,8,10,12-hexaazaisowurtzitane" describes the synthesis of the compound named in the title. This compound is hereinafter referred to as HBIW. The more formal chemical name for this compound is 2,4,6,8,10,12-hexabenzyl-2,4,6,8,10,12-hexaazatetracyclo-[5.5.0.0.$^{3,11}$ 0.$^{5,9}$]dodecane. Nielsen et al. in documents entitled "Polynitropolyaza Caged Explosives Parts 5 & 6" (Part 6 is classified) and "synthesis of a caged nitramine" (classified) prepared for the Naval Weapons Center, China Lake, Calif., describe the synthesis of 2,4,6,8,10,12-hexanitro-2,4,6,8,10,12-hexaayatetracyclo[5.5.0.0.$^{3,11}$ 0.$^{5,9}$]dodecane which is known in the propellent/explosives field as CL-20 (This compound is hereinafter referred to as CL-20). The above-identified works of Nielsen and Nielsen et al. are incorporated herein by reference.

CL-20 is an oxidizer with great potential for use in high-energy compositions, such as propellants, gassifiers, explosives or the like. CL-20 has high detonation velocity attributable to its high heat of formation. It is also advantageous because of its high density, which is a result of the cage structure. It has particular usefullness for minimum smoke formulations (generally non-aluminized formulations). It also has particular usefulness in explosive compositions.

HBIW has the following chemical structure; the indicated numbering of the carbon and nitrogen ring member are understood to apply throughout the specification:

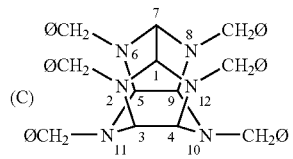

(I)

It is to be noted in the above formula that the identical 2, 6, 8, and 12 cage nitrogens are members of 5 and 6 member rings, whereas the 4 and 10 cage nitrogens are members of 6 and 7 member rings. It is found that in many chemical reactions, the four identical nitrogens react differently than the two identical nitrogens. These different nitrogens will be referred to hereinafter as the 2-6-8-12 nitrogens or the 4–10 nitrogens, respectively.

CL-20 has the following chemical structure:

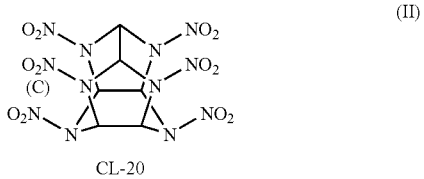

(II)

In the first step of the procedure of converting HBIW (I) to CL-20 (II), HBIW is converted to 2,6,8,12-tetraacetyl-4,10-dibenzyl-hexaazaisowurtzitane, hereinafter referred to as compound IIIA, (also referred to herein as TADB) having the formula shown below:

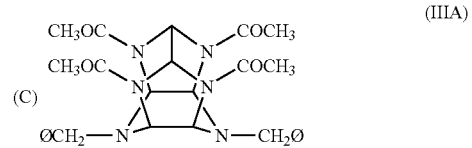

(IIIA)

The transformation from HBIW (I) to Compound IIIA is effected, for example, with hydrogen in the presence of a palladium hydroxide-on-carbon catalyst and acetic anhydride using a bromobenzene catalyst. Subsequent conversion of Compound (IIIA) to CL-20 is effected using, in succession, the nitrating agents NOBF$_4$ and NO$_2$BF$_4$. These nitrating agents are very expensive. Also because of the fluorine present, waste products pose significant environmental problems. The expense of producing CL-20 by this synthesis is a significant limitation to its general usefullness in the propellant and explosive industries.

Accordingly, it is a general object of the invention of provide methods of syntheses of CL-20 and related energetic compounds, which methods are an improvement from the standpoint of cost and environmental impact. It is further an object of the invention to provide novel chemical intermediates which can be converted to CL-20 and related high-energy caged nitrogen compounds.

SUMMARY OF THE INVENTION

In accordance with the invention, HBIW (Compound I) is chemically converted to an intermediate compound having the general formula:

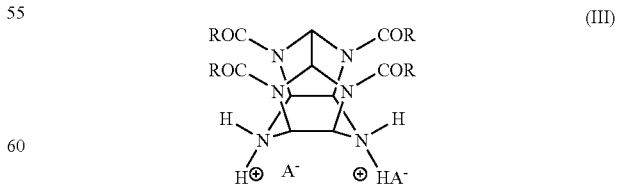

(III)

where the R's are the same or different and are selected from the group consisting of alkyl, cycloalkyl, aryl, arylalkyl, alkene, alkyne, substituted forms of any of these groups, e.g. with halogens or nitro groups, or H; a group consisting of (H⁺A⁻) (a hydrogen ion and a complementary anion); present on neither, one or both of the 4 and 10 nitrogens. Equivalently divalent anions may complement the H⁺ ions on the two 4 and 10 nitrogens. Compounds of general formula (IV) may be produced, for example, by first converting HBIW to compound IIIA by the referenced method of A. T. Nielsen supra. and then converting compound IIIA a compound of formula (IV) by catalytic transfer hydrogenolysis.

Compounds of formula (IV) may be nitrated to produce a compound of the formula:

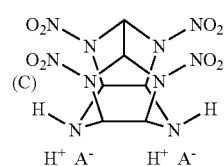

(V)

in which a group (H⁺A⁻) is present on neither, one or both of the 4 and 10 nitrogens. Compounds of formula (V) having two (H⁺A⁻) groups (the bits salt) and in which A⁻ is an energetic anion, such as $NO_2^-$ or $ClO_4^-$ are useful high energy compounds.

Compounds of formula (IV) may also be reacted with an acylating agent, such as an acid anhydride or an acid chloride, to produce a hexaamide of the following formula:

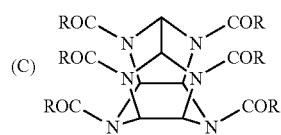

(VI)

where the R's are the same or different and are selected from the group consisting of alkyl, cycloalkyl, aryl, arylalkyl, alkene, alkyne, substituted forms of any of these groups, e.g. with halogens or nitro groups, or H.

Compounds of formula (VI) may be converted by nitrolysis nitration to CL-20 using a strong nitrating agent.

DETAILED DESCRIPTION OF CERTAIN PREFERRED EMBODIMENTS

Generally in accordance with the improved synthesis of CL-20, HBIW formula is chemically transformed to a hexaamide of formula (VI). A hexaamide of formula (VI) can be reacted with a strong nitrating agent, such as $N_2O_5$ in nitric acid or a nitric acid/sulfuric acid mixture, to produce CL-20. These nitrating agents are much less expensive than $NOBF_4$ and $NO_2BF_4$, heretofore required in the above referenced method of A. T. Nielsen et al. for producing CL-20. HBIW is a known compound and its synthesis will not be described further herein. It is understood that equivalents of HBIW (I) might also be used, e.g., HBIW (I) with substitutions on one or more of the aromatic rings.

The presently preferred route for transforming HBIW to a compound of formula (VI) is to first convert HBIW to a compound of formula (III) by the above-referenced method of A. T. Nielsen et al.; formula (III) is as follows:

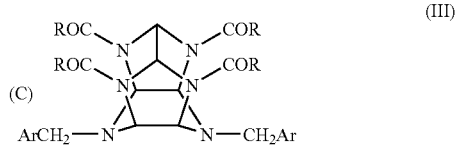

(III)

where the R's are the same or differ and are selected from the group consisting of alkyl, cycloalkyl, aryl, arylalkyl, alkene, alkyne, substituted forms of any of these groups, or H. (Compound (IIIA) is the compound of Formula (III) wherein all four R's are $CH_3$ and Ar is phenyl). Ar is generally a phenyl group, although another aromatic group, substituted or unsubstituted, is considered to be equivalent.

Compounds of formula (III) are converted to compounds of general formula (IV) by hydrogenolysis. At the present time, a catalytic transfer hydrogenolysis is used. Catalytic transfer hydrogenolysis and reagents and catalysts therefore are described, for example, in (R. A. W. Johnstone et al. *Chem Rev.*, 85, 129–170 (1985)), the teachings of which are incorporated herein by reference. One useful method of effecting the catalytic transfer hydrogenolysis is using formic acid as the hydrogen donor in the presence of a palladium-on-carbon catalyst. The formic acid is generally used in a large molar excess, e.g., as the solvent for the reaction. Depending upon the reaction conditions used, a compound of formula (IV) is produced which is the bis salt (two (H⁺A⁻) groups (A here being formate anion)), the mono formate salt or the free base. It is found that if formic acid is used neat with the Pd/C catalyst, the bis salt tends to be produced, a mixed water/formic acid solvent system tends to produce the mono salt; and a formic acid/methanol solvent system tends to produce the free base. Synthesis of the free base is often preferred to synthesis of either the bis or the mono salt; however, synthesis of the free base is less reproducible than synthesis of the bis or mono salt.

These reactions are exemplified as follows:

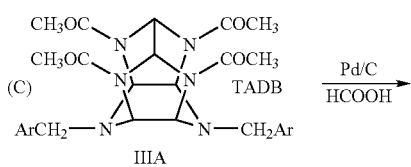

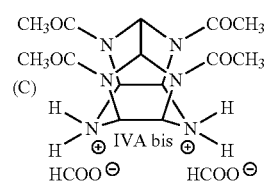

BIS SALT

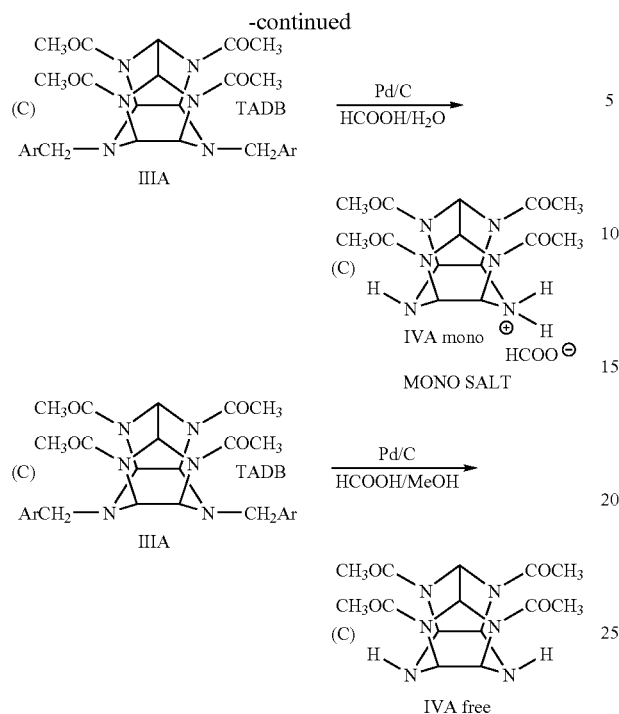

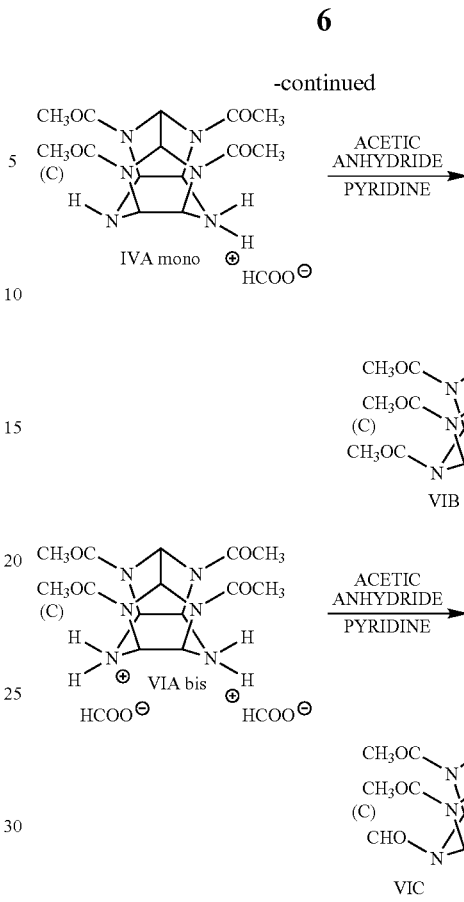

The novel compounds of formula (IV) are important intermediates for the production of CL-20 or for compounds of formula (V).

The bis or mono salts of formula (IV) may be converted to the free base by reaction with a strong base, such as an aqueous sodium hydroxide solution or a strongly basic anionic exchange resin, e.g., Dowex-50$^R$ in the OH form.

The 4 and 10 nitrogens of compounds of formula (IV) may be converted to hexaamide compounds of formula (VI) by reaction with an acylating agent, such as acid anhydride in the presence of a basic catalyst, such as pyridine. An acyl halide may alternatively be used as the acylating agent. If the free base is used, the reaction of the 4–10 nitrogens is a straight-forward acylation. If the bis or mono salt formats is acylated with acetic anhydride, the corresponding bis or mono N-formyl compound is obtained. Thus acylation using acetic anhydride of bis formats salt, mono formats salt and free base of formula (IV) compounds are compared in the following reactions:

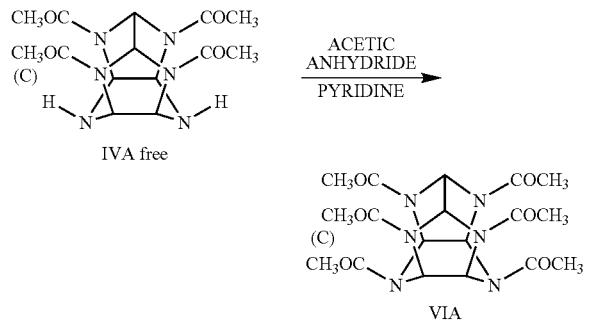

Although the products of each reaction is slightly different, each of the products is of general formula (VI). Compounds of formula (VI) are likewise important intermediates in the synthesis of CL-20.

Compounds of Formula (VI) are converted to CL-20 with strong nitrating agents which produce nitramine groups at the 2,4,6,8,10 and 12 positions on the cage structure. Suitable agents include, but are not limited to $N_2O_5$ in nitric acid or a nitric acid/sulfuric acid mixture. This reaction is as follows:

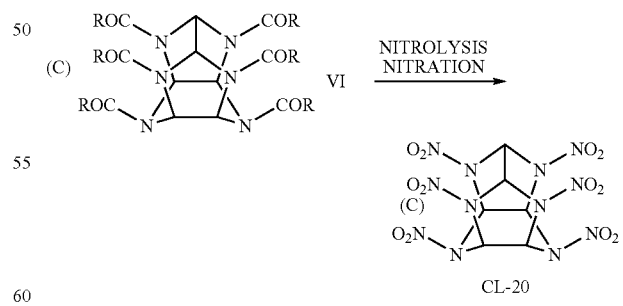

As mentioned above, Compounds of formula (IV) can also be converted to compounds of formula (V) by nitrolysis nitration by reaction with a strong nitrating agent, such as $N_2O_5$/nitric acid, or nitric acid/sulfuric acid, to produce a compound of formula (V). Subsequent reaction with an acid having an energetic anion, such an NO$_3$ or ClO$_4$, yields a highly energetic compound of formula V. These reactions are as follows:

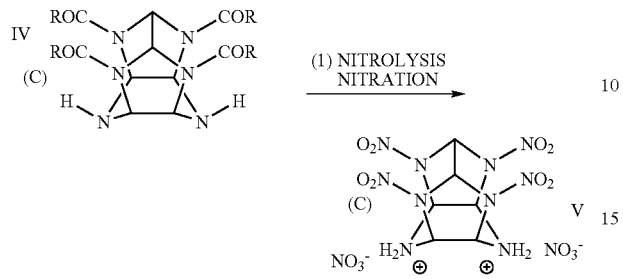

Nitrolysis nitration of a compound of formula IV may also produce some CL-20.

Compounds of formula V are most energetic in the form of bis salts of energetic anions, such as NO$_3^-$ or ClO$_4^-$. The nitration reaction produces the bis nitrate salt. To achieve a more energetic salt, the nitrate salt may be converted to a free base, e.g., by reaction with a base such as NaOH, and subsequently reacted with an acid having the energetic anion. Alternatively, the nitrate salt may be converted to a more energetic salt directly with an appropriate anion exchange resin.

As an alternative method of converting a compound of formula (IV) to CL-20, the compound is reacted with a nitrite, e.g., sodium nitrite in an aqueous acid, to produce a compound of the formula VII as shown in the following reaction.

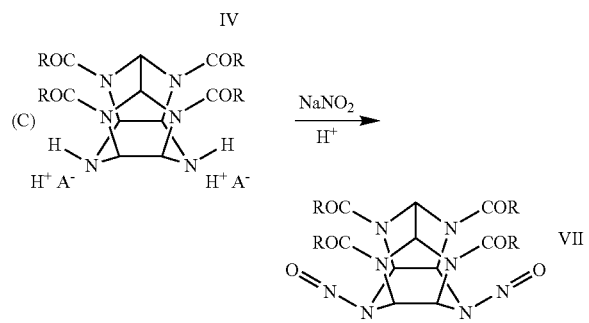

This compound VII, when nitrated with a strong nitrating agent, such as N$_2$O$_5$ in nitric acid or a nitric acid/sulfuric acid mixture, undergoes a nitrolysis nitration reaction to produce CL-20 as follows:

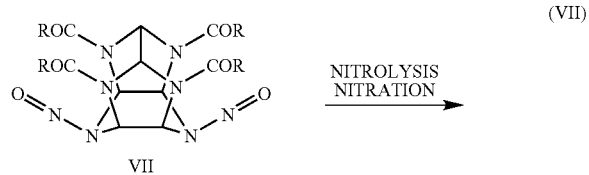

-continued

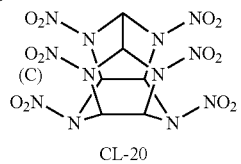

The invention will now be described in greater detail by way or specific examples.

EXAMPLE 1

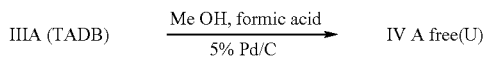

To a stirred slurry of 48.0 mg (0.093 mmole) of TADB in 4 ml of methanol and 0.2 ml of formic acid were added 51 mg of 5% Pd/C. The reaction was warmed to 40°–60° C. for 18 hours. The Pd/C and product were removed by filtration. Extraction of the Pd/C with DMSO afforded the desired product.

$^1$H NMR (DMSO): (δ)1.8.2.1 (multiplet, 12H, CH$_3$CO), 4.02–4.25 (multiplet, 2H, NH), 5.2–5.3 (multiplet, 4H, CH), 6.0–6.5 (multiplet, 2H, CH).

Upon heating to 150° C., the multiplet at 1.8.21, collapses to a singlet at 2.0, the multiplet at 4.02–4.25 collapses to a singlet at 3.7, the multiplet at 5.2–5.3 collapses to a singlet at 5.3 and the multiplet at 6.0–6.5 collapses to a singlet at 6.3.

EXAMPLE 2

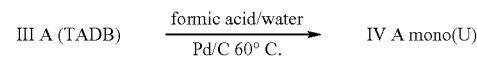

To a vigorously stirred solution of 10.0 (19.36 mmole) of TADB in 200 ml of water were added 40 ml of formic acid; then 10.0 g of 5% Pd/C was added. The reaction was warmed to 60° C. After 18½ hr, the solids were filtered away from the solution and the volatiles were removed under reduced pressure to afford 7.9 g (106.7×) of mono formate salt.

$^1$H NMR (DMSO): (δ) 7–2.3 (multiplet, 12H, CH$_3$CO), 4.7–4.9 (broad double, 1H, NH, J=9.0 Hz), 5.5–5.7 (multiplet, 2H, CH), 6.0–6.8 (multiplet, 4H, CH), 8.3 (broad singlet, 4H, NH, HCO$_2$H).

Upon heating to 150° C., the multiplet at 1.1–2.3 collapses to 2s, the bd at 4.7–4.9 moves to 4.3 and broadens, the multiplet at 5.5–5.7 collapses to a doublet at 5.6 (J=6 Hz), and the broad singlet at 8.3 splits into 2 singlets at 8.32 and 8.39.

EXAMPLE 3

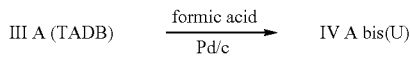

To a stirred slurry of 10.09 (19.36 mmol) of TADB in 200 ml of formic acid were added 10.0 g of 5% Pd/C. After 18 hours, the Pd/C was removed by filtration and the formic acid was removed under reduced pressure to afford 8.78 g (104%) of the desired bis salt.

$^1$H NMR (DMSO): 1.9–2.2 (multiplet, 12H, CHICO), 6.1–6.8 (multiplet, 6H, CH), 8.1–8.4 (multiplet, 6+H, NH, HCO$_2$H).

Upon heating to 150° C., the multiplet at 1.9–2.2 collapses to a singlet and the other 2 multiplets begin to collapse.

EXAMPLE 4

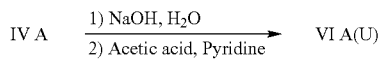

To 500 mg (1.17 mmol) of bis formate salt were added 2.4 ml of 1M NaOH). All volatiles were removed under reduced pressure. The residue was dissolved in 20 ml of acetic anhydride and 5 ml of pyridine and heated at 60° C. overnight. After 18 hours, the volatiles were removed and the residue treated with 10 ml of EtOAc. The solution was filtered and concentrated. The residue was passed through a plug of silica gel using acetone as eluent giving VI A as an impure solid.

$^1$H NMR (CHCl$_3$): (δ)2.05–2.2 (multiplet, 12H, CH$_3$CO), 2.45 (singlet, 6H, CH$_3$CO), 6.3–6.5 (multiplet, 4H, CH), 6.8–7.0 (multplet, 2H, CH).

Upon heating to 150° C. (DMSO solvent), the multiplet at 2.05–2.2 collapses to a singlet. The multiplet at 6.3–6.5 and 6.8–7.0 each begin to collapse.

EXAMPLE 5

To a stirred slurry of 5.0 g (13.1 mmol) of mono formate salt in 200 ml of acetic anhydride were added 50 ml of pyridine. After 20 hours, all volatiles were removed under reduced pressure. Then the residue was treated with 100 ml of EtOAc. A precipitate formed which was removed by filtration. The solvent was removed and the residue passed through a plug of silica gel using acetone as eluent.

$^1$H NMR (CHCl$_3$): 2.06, 2.09, 2.12, 2.14 (4singlet, 12H, CH$_3$CO), 2.42 (singlet, 3H, CH$_3$CO), 6.0–7.0 (multiplet, 6H, CH), 8.3 (singlet, 1H, CHO).

EXAMPLE 6

To a stirred slurry of 5.0 g (11.67 mmol) of bis formate salt (IV A bis) in 200 ml of acetic anhydride were added 50 ml of pyridine. After 20 hours, all volatiles were removed under reduced pressure. Then the residue was treated with 100 ml of EtOAc. A precipitate formed which was removed by filtration. The solvent was removed and the residue passed through a plug of silica gel using acetone as eluent. Obtained was 4.5 g (98.3%) yield of bis formyl compound. R$_f$=0.35 (acetone).

$^1$H NMR (CHCl$_3$): (δ)2.0–2.3 (multiplet, 12H, CH$_3$CO), 6.06 (doublet, 0.2H, CH, J=4.8 Hz), 6.15 (broad singlet, 0.45H, CH), 6.26 (doublet, 1.5H, CH, J=7.8, 1.8 Hz), 6.46 (singlet, 1.7H, CH), 6.67 (doublet, 1.5H, CH, J=7.8, 1.81 Hz), 6.75–6.81 (multiplet, 0.65H, CH).

EXAMPLE 7

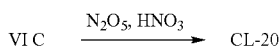

To 10 mg (0.026 mmol) of diformyl tetraacetyl compound VI C were added 2 ml of 5% N$_2$O$_5$ in nitric acid at 0° C. for 4.5 hours; the mixture was then diluted with water. The aqueous solution was extracted 4× with ethyl acetate. The organics were dried (MgSO$_4$) and concentrated to dryness. By this layer chromatography (silica gel, multiple solvent systems). The product exhibited an R$_f$ identical to CL-20 and a superimpossable $^1$H NMR spectrum.

EXAMPLE 8

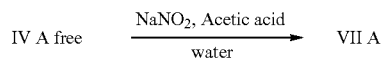

To 1.0 g of tetraactyl (IV A free) in 2 ml of water and 2 ml of acetic acid were added 0.70 g of NaNo$_2$ in 2 ml of water at OC. Stirred 18 hours at room temperature. The desired product precipitated from the reaction mixture and was collected by filtration in a quantitative yield.

While the invention has been described in terms of certain preferred embodiments, modifications obvious to one with ordinary skill in the art may be made without departing from the scope of the present invention.

Various features of the invention are set forth in the following claims.

What is claimed is:

1. A compound selected from the group consisting of

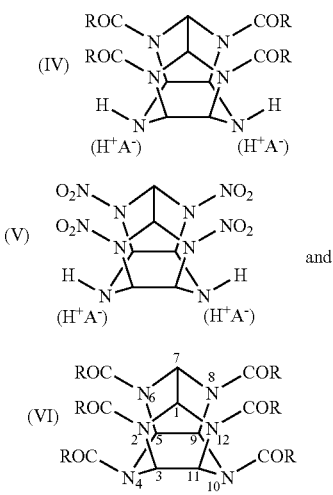

wherein each of the "R's" is the same or different and is selected from the group consisting of alkyl, cycloalkyl, aryl, arylalkyl, alkene, alkyne, substituted forms of any of these groups, and H, and wherein a group consisting of a hydrogen ion ($H^+$) and a complementary anion is present on neither, one, or both of the nitrogens in the 4 and 10 positions.

2. The compound of claim 1, wherein the compound is formula (IV).

3. The compound of claim 2 wherein all R's are $CH_3$.

4. The compound of claim 1 wherein the compound is formula (V).

5. The compound of claim 4 wherein the compound comprises a hydrogen ion and an anion associated with the nitrogen in each of the 4 and 10 positions, the anion being an energetic anion.

6. The compound of claim 5 wherein the anion is $NO_3^-$ or $ClO_4^-$.

7. The compound of claim 1 wherein the compound is formula (VI) and wherein all R's are $CH_3$ or H.

8. A method of preparing a compound of formula IV:

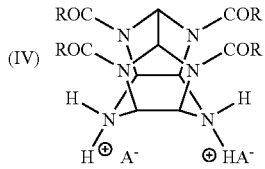

wherein each R is independently selected from the group consisting of alkyl, cycloalkyl, aryl, arylalkyl, alkene, alkyne, a substituted form of any of these groups, and H, and wherein a member from the group consisting of a hydrogen anion and a complementary anion is present on neither, one, or both of the nitrogens in the 4 and 10 positions, the method comprising:

hydrogenolyzing a compound of formula III:

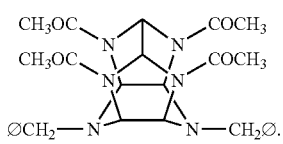

9. The compound of claim 2, wherein the compound is represented by the formula:

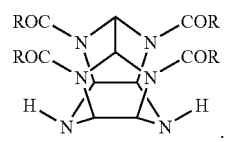

10. The compound of claim 2, wherein the compound has a group consisting of a hydrogen atom and a complementary anion associated with the nitrogen in each of the 4 or 10 positions.

11. The compound of claim 2, wherein the compound has a group consisting of a hydrogen atom and a complementary anion associated with the nitrogen in each of the 4 and 10 positions.

12. The compound of claim 10, wherein the complementary anion is an energetic anion.

13. The compound of claim 11, wherein each complementary anion is an energetic anion.

14. The compound of claim 4, wherein the compound is represented by the formula:

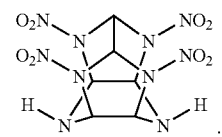

15. The compound of claim 4, wherein the compound has a group consisting of a hydrogen atom and a complementary anion associated with the nitrogen at the 4 or 10 positions, and wherein each complementary anion is an energetic anion.

* * * * *

UNITED STATES PATENT AND TRADEMARK OFFICE
CERTIFICATE OF CORRECTION

| | | |
|---|---|---|
| PATENT NO. | : 7,129,348 B1 | |
| APPLICATION NO. | : 07/292028 | |
| DATED | : October 31, 2006 | |
| INVENTOR(S) | : Robert B. Wardle et al. | |

It is certified that error appears in the above-identified patent and that said Letters Patent is hereby corrected as shown below:

On the title page:
In ITEM (56) References Cited
OTHER PUBLICATIONS

Page 1, 1st column, 3rd line of the
1st entry — change "Lake C." to --Lake, CA.--

Page 1, 2nd column, 2nd line of the
2nd entry — change "Hexaazaisowurtzitan" to --Hexaazaisowurtzitane--

Page 1, 2nd column, 3rd line of the
2nd entry — change "Lake CA." to --Lake, CA.--

Page 1, 2nd column, 2nd line of the
5th entry — change "Hexanitrohexaazalsowurtzitane,""" to --Hexanitrohexaazaisowurtzitane,"--

Page 1, 2nd column, 2nd line of the
9th entry — change "Y-Hexanitrohexaazalsowurtzitane," j." to --Y-Hexanitrohexaazaisowurtzitane," J.--

In ITEM (57) ABSTRACT

Page 1, 2nd column, line 1 — change "tetracetyl" to --tetracetyl,--
Page 1, 2nd column, line 2 — change "dibenzyl azaisowurtzitane." to --dibenzyl-azaisowurtzitane.--
Page 1, 2nd column, line 3 — change "hydrogenolysis leaving" to --hydrogenolysis, leaving--

In the specification:

COLUMN 1, LINE 23, change " "synthesis" to --"Synthesis--
COLUMN 1, LINE 26, change "12-hexaayatetracyclo" to --12-hexaazatetracyclo--
COLUMN 2 LINE 34, change "Also because" to --Also, because--

Signed and Sealed this
First Day of November, 2011

David J. Kappos
*Director of the United States Patent and Trademark Office*

CERTIFICATE OF CORRECTION (continued)
U.S. Pat. No. 7,129,348 B1

In the specification (continued):

| | | |
|---|---|---|
| COLUMN 2, | LINE 39, | change "is a general object of the invention of" to --would be desirable to-- |
| COLUMN 2, | LINE 40, | change "syntheses of" to --synthesizing-- |
| COLUMN 2, | LINES 42, 43, | change "is further an object of the invention" to --would also be desirable-- |
| COLUMN 2, | LINES 43, 44, | change "intermediates which" to --intermediates, which-- |
| COLUMN 2, | LINE 64, | change "where the R's are" to --where each of the "R's" is-- |
| COLUMN 2, | LINE 64, | change "and are" to --and is independently-- |
| COLUMN 2, | LINE 67, | change "or H; a" to --and H; and a-- |
| COLUMN 3, | LINE 2, | change "one or" to --one, or-- |
| COLUMN 3, | LINE 7, | change "supra." to --(*supra*)-- |
| COLUMN 3, | LINE 23, | change "one or" to --one, or-- |
| COLUMN 3, | LINES 26, 27 | change "$ClO_4^-$" are useful high energy" to --$ClO_4^-$, are useful high-energy-- |
| COLUMN 3, | LINE 42, | change "where the R's are" to --where each of the "R's" is-- |
| COLUMN 3, | LINE 42, | change "and are" to --and is-- |
| COLUMN 3, | LINE 45, | change "e.g." to --e.g.,-- |
| COLUMN 3, | LINE 45, | change "or H." to --and H.-- |
| COLUMN 4, | LINE 2, | change "et al.; formula" to --et al. Formula-- |
| COLUMN 4, | LINE 13, | change "where the R's are the same or differ and are" to --where each of the "R's" is the same or different and is-- |
| COLUMN 4, | LINE 15, | change "groups, or" to --groups, and-- |
| COLUMN 4, | LINE 17, | change "R's are" to --"R's" are-- |
| COLUMN 4, | LINE 25, | change "et al." to --et al.,-- |
| COLUMN 4, | LINE 35, | change "produced which" to --produced, which-- |
| COLUMN 4, | LINE 37, | change "salt or" to --salt, or-- |
| COLUMN 4, | LINE 39, | change "produced, a" to --produced; a-- |
| COLUMN 5, | LINE 46, | change "formats" to --formate-- |
| COLUMN 5, | LINE 49, | change "of bis formats salt, mono formats salt and" to --of the bis formate salt, mono formate salt, and-- |
| COLUMN 6, | LINE 36, | change "is slightly" to --are slightly-- |
| COLUMN 6, | LINE 42, | change "agents which" to --agents, which-- |
| COLUMN 6, | LINE 43, | change "2,4,6,8,10 and" to --2,4,6,8,10, and-- |
| COLUMN 6, | LINE 44, | change "to $N_2O_5$" to --to, $N_2O_5$-- |
| COLUMN 6, | LINE 64, | change "Compounds" to --compounds-- |
| COLUMN 6, | LINE 67, | change "acid, or" to --acid or-- |
| COLUMN 7, | LINE 2, | change "such an $NO_3$ or $C1O_4$," to --such as $NO_3^-$ or $C1O_4^-$,-- |

CERTIFICATE OF CORRECTION (continued)
U.S. Pat. No. 7,129,348 B1

In the specification (continued):

| | | |
|---|---|---|
| COLUMN 8, | LINE 12, | change "way or" to --way of-- |
| COLUMN 8, | LINE 19, | change "IV A free(U)" to --IV A free-- |
| COLUMN 8, | LINE 23, | change "mmole)" to --mmol)-- |
| COLUMN 8, | LINE 30, | change "1.8.2.1" to --1.8-2.1-- |
| COLUMN 8, | LINE 33, | change "1.8.21," to --1.8-2.1-- |
| COLUMN 8, | LINE 45, | change "IV A mono(U)" to --IV A mono-- |
| COLUMN 8, | LINE 49, | change "mmole)" to --mmol)-- |
| COLUMN 9, | LINE 5, | change "IV A bis(U)" to --IV A bis-- |
| COLUMN 9, | LINE 15, | change "6+H," to --6H,-- |
| COLUMN 9, | LINE 27, | change "VI A(U)" to --VI A-- |
| COLUMN 9, | LINE 60, | change "Then the" to --Then, the-- |
| COLUMN 9, | LINE 61, | change "formed which" to --formed, which-- |
| COLUMN 10, | LINE 12, | change "Then the" to --Then, the-- |
| COLUMN 10, | LINE 13, | change "formed which" to --formed, which-- |
| COLUMN 10, | LINE 15, | change "as eluent." to --as the eluent.-- |
| COLUMN 10, | LINE 44, | change "systems). The" to --systems), the-- |
| COLUMN 10, | LINE 45, | change "superimpossable" to --superimposable-- |
| COLUMN 10, | LINE 57, | change "Stirred" to --The reaction mixture was stirred-- |

In the claims:

| | | | |
|---|---|---|---|
| CLAIM 2, | COLUMN 11, | LINE 33, | change "compound is" to --compound comprises-- |
| CLAIM 4, | COLUMN 11, | LINE 36, | change "compound is" to --compound comprises-- |
| CLAIM 6, | COLUMN 11, | LINE 42, | change "claim 5" to --claim 5,-- |
| CLAIM 7, | COLUMN 11, | LINE 44, | change "compound is" to --compound comprises-- |